US009414601B2

(12) United States Patent
Code

(10) Patent No.: US 9,414,601 B2
(45) Date of Patent: *Aug. 16, 2016

(54) MATERIAL HAVING ANTIMICROBIAL ACTIVITY WHEN WET

(75) Inventor: Kenneth R. Code, Edmonton (CA)

(73) Assignee: BIOLARGO LIFE TECHNOLOGIES, INCORPORATED, Irvine, CA (US)

(*) Notice: Subject to any disclaimer, the term of this patent is extended or adjusted under 35 U.S.C. 154(b) by 1510 days.

This patent is subject to a terminal disclaimer.

(21) Appl. No.: 12/220,484

(22) Filed: Jul. 24, 2008

(65) Prior Publication Data

US 2009/0028915 A1 Jan. 29, 2009

Related U.S. Application Data

(63) Continuation-in-part of application No. 11/973,933, filed on Oct. 11, 2007, now Pat. No. 8,021,610, which is a continuation-in-part of application No. 11/516,960, filed on Sep. 7, 2006, now Pat. No. 7,867,510, and a continuation-in-part of application No. 11/516,958, filed on Sep. 7, 2006, now abandoned.

(60) Provisional application No. 60/961,903, filed on Jul. 25, 2007, provisional application No. 60/850,976, filed on Oct. 11, 2006.

(51) Int. Cl.
A01N 59/12 (2006.01)
A01N 25/08 (2006.01)
A01N 25/34 (2006.01)

(52) U.S. Cl.
CPC .............. A01N 59/12 (2013.01); A01N 25/08 (2013.01); A01N 25/34 (2013.01)

(58) Field of Classification Search
CPC ....... A01N 59/12; A01N 25/26; A01N 25/00; A01N 25/12; C02F 2303/04
See application file for complete search history.

(56) References Cited

U.S. PATENT DOCUMENTS

| 206,024 | A | 7/1878 | Kendall | 222/432 |
|---|---|---|---|---|
| 2,134,791 | A | 11/1938 | Loweke | 188/79.53 |
| 3,464,413 | A | 9/1969 | Goldfarb et al. | 604/306 |
| 3,489,148 | A | 1/1970 | Duncan et al. | 604/382 |
| 3,585,998 | A | 6/1971 | Hayford et al. | 165/8 |
| 3,708,263 | A | 1/1973 | Boucher | 422/20 |
| 3,800,792 | A | 4/1974 | McKnight et al. | 602/50 |
| 3,896,807 | A | 7/1975 | Buchalter | 604/289 |
| 4,131,645 | A | 12/1978 | Keblys et al. | 423/501 |
| 4,375,535 | A | 3/1983 | Kightlinger et al. | 527/313 |
| 4,381,784 | A | 5/1983 | Aberson et al. | 604/368 |
| 4,405,323 | A | 9/1983 | Auerbach | 604/285 |
| 4,418,686 | A | 12/1983 | Child | 604/285 |
| 4,497,930 | A | 2/1985 | Yamasaki et al. | 524/556 |
| 4,675,014 | A | 6/1987 | Sustmann et al. | 604/375 |
| 4,715,965 | A | 12/1987 | Sigerson et al. | 210/511 |
| 4,722,937 | A | 2/1988 | Jacob et al. | 514/474 |
| 4,731,391 | A | 3/1988 | Garvey | 521/137 |
| 4,888,118 | A | 12/1989 | Barnes et al. | 210/668 |
| 5,019,495 | A | 5/1991 | Shanbrom | 435/1.1 |
| 5,128,149 | A | 7/1992 | Shanbrom | 424/529 |
| 5,128,150 | A | 7/1992 | Shanbrom | 424/533 |
| 5,176,836 | A | 1/1993 | Sauer et al. | 210/670 |
| 5,186,945 | A | 2/1993 | Shanbrom | 424/529 |
| 5,201,326 | A | 4/1993 | Kubicki et al. | 128/832 |
| 5,227,161 | A | 7/1993 | Kessler | 424/94.4 |
| 5,265,302 | A | 11/1993 | Sivacoe | 15/104.061 |
| 5,324,438 | A | 6/1994 | McPhee et al. | 210/748 |
| 5,356,611 | A | 10/1994 | Herkelmann et al. | 423/501 |
| 5,360,605 | A | 11/1994 | Shanbrom | 424/78.08 |
| 5,370,869 | A | 12/1994 | Shanbrom | 424/78.22 |
| 5,384,929 | A | 1/1995 | Smith | 15/104.061 |
| 5,419,902 | A | 5/1995 | Kessler | 424/94.4 |
| 5,464,603 | A | 11/1995 | Marchin et al. | 423/501 |
| 5,552,051 | A | 9/1996 | Wang et al. | 210/604 |
| 5,589,072 | A | 12/1996 | Shanbrom | 210/638 |
| 5,609,864 | A | 3/1997 | Shanbrom | 424/78.08 |
| 5,612,045 | A | 3/1997 | Syverson | 424/402 |

(Continued)

FOREIGN PATENT DOCUMENTS

| DE | DE 2029 598 | 12/1970 | |
|---|---|---|---|
| EP | 439 878 | 8/1991 | .............. C11D 17/00 |
| EP | 446 761 | 9/1991 | .............. C11D 3/395 |
| EP | 611 206 | 8/1994 | .............. C11D 17/00 |
| GB | 2344997 | 6/2000 | .............. A01N 25/30 |
| WO | WO92/09289 | 6/1992 | ........... A61K 31/765 |
| WO | WO93/21299 | 10/1993 | .............. C11D 17/00 |
| WO | WO02/08126 | 1/2002 | |

OTHER PUBLICATIONS

P. Kapur and M. Verma, "Determination of Iodate Ion in Presence of Cupric Ion", Industrial and Engineering Chemistry Analytical Ed.; vol. 13, No. 5 (May 1941). p. 338.

M. Abdalla, et al., *Ioddimetric Determination of Iodate, Bromate, Hypochlorite, Ascorbic Acid and Thiourea Using Flow Injection Amperometry*. Dept of Chem, College of Sri, King Saad Univ, Saudi Arabia Analyst, May 1989, vol. 114, p. 583-586, especially p. 583.

Foret, et al., *The Effect of Free Iodine on the Germicidal Activity of Iodine Teat Dips*. Milkproduction.com, Dec. 12, 2002., Especially Tables 103.

PCT International Search Report and the Written Opinion of the Internatoinal Searching Authority dated Sep. 18, 2009, from related patent application PCT/US2009/04248.

Primary Examiner — Kyle Purdy
(74) Attorney, Agent, or Firm — Mark A. Litman & Associates, P.A.

(57) ABSTRACT

An article is applied to the surface of an article, animal housing environment or animal (including humans) to provide antimicrobial activity when activated with a liquid comprising alcohol. The article may comprise a water and/or alcohol absorbent material; and a composition that reacts with water and/or alcohol to produce molecular iodine. The composition provides a local concentration (in the water and/or alcohol) of at least 5 or 10 parts per million iodine in water and/or alcohol carried by the material (that is actual water supported by the water absorbent material) when the material has 5% by weight of water present in the water absorbent.

15 Claims, 1 Drawing Sheet

(56) References Cited

U.S. PATENT DOCUMENTS

| | | | |
|---|---|---|---|
| 5,629,024 A | 5/1997 | Kessler et al. | 424/667 |
| 5,635,063 A | 6/1997 | Rajan et al. | 210/266 |
| 5,639,452 A | 6/1997 | Messier | 424/78.1 |
| 5,639,481 A | 6/1997 | Kessler et al. | 424/667 |
| 5,643,588 A | 7/1997 | Roe et al. | 424/402 |
| 5,648,075 A | 7/1997 | Kessler et al. | 424/94.4 |
| 5,772,971 A | 6/1998 | Murphy et al. | 422/292 |
| 5,849,291 A | 12/1998 | Kessler | 424/94.4 |
| 5,885,592 A | 3/1999 | Duan et al. | 424/400 |
| 5,903,946 A | 5/1999 | Collins et al. | 15/104.061 |
| 5,919,374 A | 7/1999 | Harvey et al. | 210/753 |
| 5,924,158 A | 7/1999 | Watts | 15/104.061 |
| 5,948,385 A | 9/1999 | Chapman et al. | 424/1.29 |
| 5,962,029 A | 10/1999 | Duan et al. | 424/613 |
| 6,004,465 A | 12/1999 | Uhr et al. | 210/651 |
| 6,037,019 A | 3/2000 | Kooyer et al. | 427/598 |
| 6,067,682 A | 5/2000 | Rankin | 15/104.061 |
| 6,071,415 A | 6/2000 | Frommer et al. | 210/669 |
| 6,139,731 A | 10/2000 | Harvey et al. | 210/175 |
| 6,146,725 A | 11/2000 | Code | 428/35.2 |
| 6,235,270 B1 * | 5/2001 | Ishii et al. | 424/59 |
| 6,248,335 B1 | 6/2001 | Duan et al. | 424/400 |
| 6,261,577 B1 | 7/2001 | Kessler | 424/401 |
| 6,328,929 B1 | 12/2001 | Code | 422/29 |
| 6,365,220 B1 | 4/2002 | Burrell et al. | 427/2.1 |
| 6,403,113 B1 | 6/2002 | Corzani | 424/404 |
| 6,403,674 B1 | 6/2002 | Schubert | 522/167 |
| 6,432,426 B2 | 8/2002 | Kessler | 424/401 |
| 6,703,536 B2 | 3/2004 | Roe et al. | 604/360 |
| 6,863,905 B1 | 3/2005 | Shanbrom | 424/667 |
| 7,000,280 B1 | 2/2006 | Knapp | 15/104.061 |
| 7,033,509 B2 | 4/2006 | Klein et al. | 210/753 |
| 7,192,911 B2 | 3/2007 | Sunder et al. | 510/223 |
| 7,431,849 B1 * | 10/2008 | Swearingen et al. | 210/749 |
| 7,867,510 B2 * | 1/2011 | Code | A61F 13/8405 424/404 |
| 2003/0135172 A1 | 7/2003 | Whitmore et al. | |
| 2004/0167048 A1 | 8/2004 | Sunder et al. | 510/220 |
| 2004/0267223 A1 | 12/2004 | Etchells | 604/385.01 |
| 2005/0196593 A1 | 9/2005 | Campbell et al. | |
| 2006/0102085 A1 | 5/2006 | Chen | 119/171 |
| 2006/0112894 A1 | 6/2006 | Ikegami et al. | 119/171 |
| 2006/0201438 A1 | 9/2006 | Anttila et al. | 119/171 |
| 2007/0039556 A1 | 2/2007 | Cook et al. | 119/166 |
| 2007/0277739 A1 | 12/2007 | Wang et al. | 119/161 |
| 2007/0289543 A1 | 12/2007 | Petska et al. | 119/173 |
| 2008/0022939 A1 | 1/2008 | Bracilovic | 119/171 |
| 2008/0058738 A1 | 3/2008 | Roberts et al. | 604/359 |
| 2008/0058739 A1 | 3/2008 | Roberts et al. | 604/359 |
| 2008/0095812 A1 | 4/2008 | Code | |

* cited by examiner

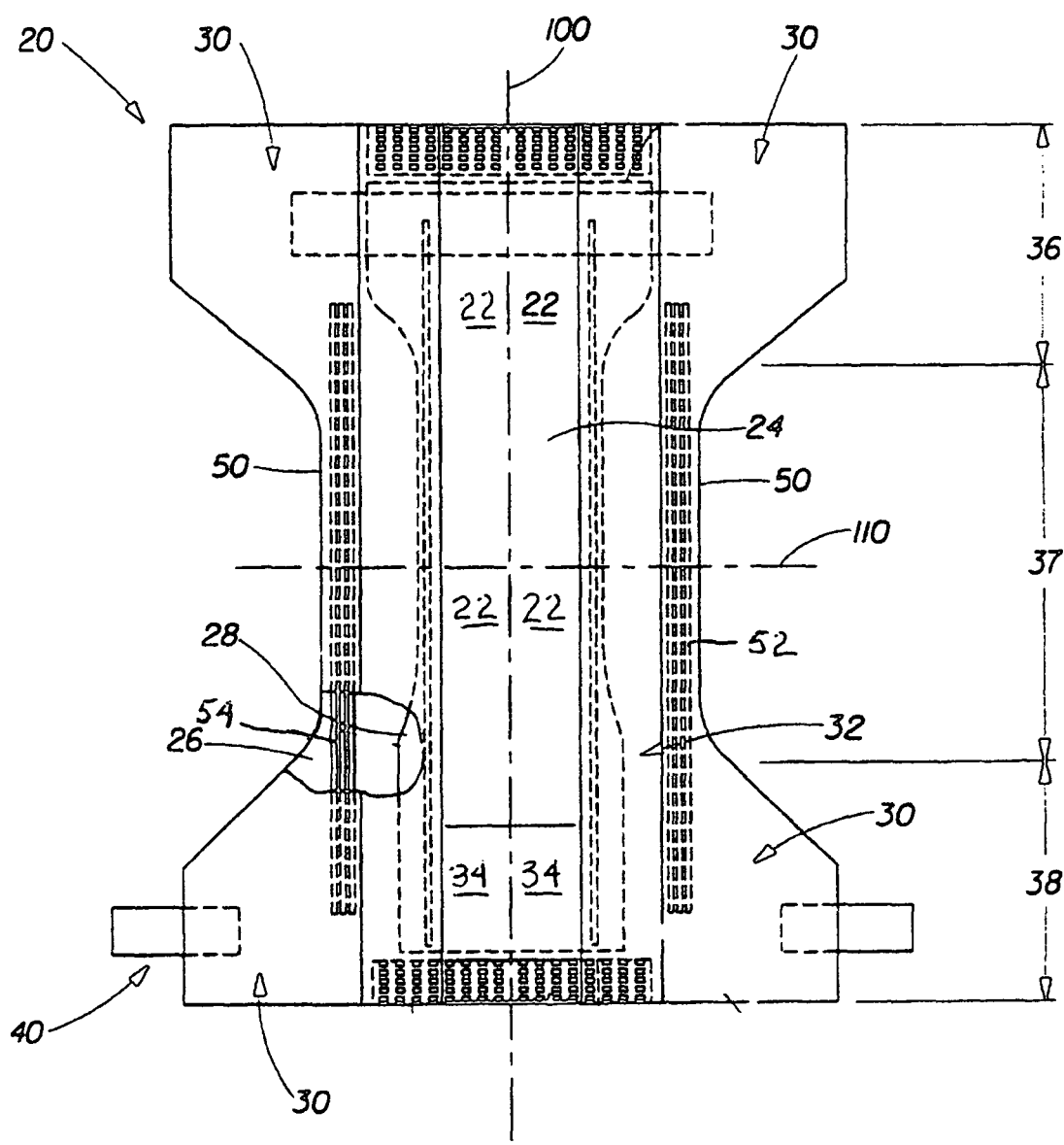

MATERIAL HAVING ANTIMICROBIAL ACTIVITY WHEN WET

RELATED APPLICATIONS DATA

This application claims priority from U.S. Provisional Application Ser. No. 60/961,903, filed Jul. 25, 2007, which in turn claims priority as a Continuation-in-Part application of U.S. Provisional Patent Application Ser. No. 60/850,976, filed Oct. 11, 2006 (now U.S. patent application Ser. No. 11/973,933) which is in turn a continuation-in-part of both of U.S. patent application Ser. No. 11/516,960, filed Sep. 7, 2006 and U.S. patent application Ser. No. 11/516,958, filed Sep. 7, 2006.

BACKGROUND OF THE INVENTION

1. Field of the Invention

The present technology relates to the field of antimicrobial protection, particularly antimicrobial activity in close proximity to hard surfaces, enclosed environments, rooms, and the bodies of patients. In particular, the field relates to the use of antimicrobial, antiodor and chemical modification agents that are active in the presence of water and/or lower molecular weight alcohols (e.g., C1-C6 alcohols).

2. Background of the Art

The growth of many microbes is assisted by or enabled by the presence of water with the microbes. Water and aqueous materials are present in events and activities of most mammalian life forms. Aqueous solutions and dispersion and emulsions are present in blood, exudates, tears, perspiration, menstrual emissions and waste emissions of mammals. These are natural events in life cycles, but may be accompanied by contact with or attack by microbes that can have significant physical effects on the animals (including humans) and their surrounding. At a minimum, growth of some microbes in aqueous materials around the animals can develop odors, disease-carrying media, infections and death or damage to the bodies of the animals.

There are many instances where aqueous materials are retained in contact with animal bodies and in which there is potential for unwanted and even dangerous and significant microbial growth or microbial introduction into the animal body. For example, in the application of materials wound dressing, menstrual products, patches, diapers, pads and the like, moisture from the animal body or ambient conditions or the materials themselves can introduce microbes to the environment and those microbes can proliferate in the vicinity of the materials when moisture is present. The uncontrolled growth of random microbes is seldom beneficial and has been the subject of significant efforts at control.

Many applications exist where it is necessary or at the very least an advantage for agents to be present which demonstrate anti-bacterial, anti-mycotic activity or both, resulting in the control of bacterial and/or fungal growth. For example, an apparatus or article as a whole or in part may have the property of suppressing bacterial and fungal growth. Control of bacterial and/or fungal growth may be through the prevention or inhibition of the growth of such microbes.

The most consistent forms of attempts at microbial control on patients are the direct application of compositions to the surfaces or volumes or patients likely to become infected. Sprays, powders, solutions and other materials have been applied directly to the affected areas as a treatment or prophylactic. These treatments generally direly apply or carry active antimicrobial materials to the site, either as a direct application of carried with a device to be secured locally to the surface.

A variety of materials are used every day in treating or preventing infections in humans, animals and the like. For example, catheters, sutures surgical gloves, implants, bandages, diapers, diaper liners, dressings, small adhesive dressings, sanitary napkins and insoles are just a few. Normally, bandages are used as a barrier to airborne pathogenic organisms infecting a cut or wound. However, once infection occurs, the bandage is no longer of any benefit. If the bandage were provided with a broad spectrum antimicrobial agent, on the portion of the bandage which is in contact with the wound and surrounding skin, the bandage becomes an actively rather than a passively antimicrobial surface or microbial barrier. Catheters, implants, bandages, dressings and other materials, such as above, are used extensively every day by millions of people. As a result, any form of antimicrobial material incorporated into these types of devices must be safe for general unsupervised use, should avoid selection of resistant strains, and should be cost effective. Furthermore, the materials may have to retain their flexibility such as with bandages so as to be readily usable. Catheters, implants, bandages, diapers, diaper liners, dressings, and the like can be readily coated with thin films of active elements which, when in contact with body fluids, release substances and ions which stop the growth of or kill various types of microorganisms. As here described, there is no requirement to apply any outside electric current to maintain sustained levels of ion release to treat the infected area.

U.S. Pat. No. 6,365,220 A process for production of an actively antimicrobial surface for a substrate and for use in a biologically dynamic environment, such as for treating and preventing microbial infections, including a film consisting of at least an antimicrobial element and another electrochemically nobler element and which forms multitudinous galvanic cells with electrolyte-containing biological fluids, such as body fluids from wounds, etc., for releasing the antimicrobial element at the surface.

WO92/09289 teaches an improved method for treating diaper rash of neonates, infants, children and incontinent adults which entails applying to the site of diaper rash a composition comprising 15-40% of a copolymer or a derivative thereof, of a lower alkyl vinyl ether and maleic acid dispersed in a semisolid ointment base.

U.S. Pat. No. 4,381,784 discloses an absorbent device designed to absorb blood or blood-like fluids such as a sanitary napkin which is combined with a blood gelling agent which includes, amongst others, maleic anhydride copolymers.

U.S. Pat. No. 6,403,113 describes that certain copolymers can be used to control or prevent the growth of microbic agents such as bacteria and fungus. It has further been found that certain derivatives of these copolymers also have anti-bacterial and anti-mycotic properties. The finding that the copolymers of the invention and derivatives thereof which are preferably of high molecular weight can be used as anti-bacterial and/or anti-mycotic agents provides many advantages over anti-microbic agents of the prior art, in particular, due to the large molecular weight and polymeric character of the anti-microbic agents of the invention. Furthermore, the copolymers or derivatives per se or blends of said copolymers or derivatives can be formed into articles or incorporated into articles in the form of films, fibers, adhesives etc. The copolymers of the invention have a low toxicity due to their high molecular weight and possess intrinsic anti-bacterial and anti-mycotic activity.

U.S. Pat. No. 6,703,536 describes an absorbent article, at least a portion of which comprises a skin care composition of an enzyme inhibitor and is at least partially transferred from the article to the skin of a wearer of the article as a result of normal contact, wearer motion and/or body heat.

The art has also used lotions in combination with absorbent articles. Examples include: U.S. Pat. No. 3,585,998 to Hayford et al.; U.S. Pat. No. 3,464,413 to Goldfarb et al.; U.S. Pat. No. 3,896,807 to Buchalter; U.S. Pat. No. 3,489,148 to Duncan et al.; and U.S. Pat. No. 5,643,588 to Roe et al.

U.S. Pat. No. 5,643,588 describes diapers having a top sheet containing lotion with Lotion compositions can comprise other optional components typically present in emollient, creams, and lotions of this type. These optional components include water, viscosity modifiers, perfumes, disinfectant antibacterial actives, pharmaceutical actives, film formers, deodorants, opacifiers, astringents, solvents and the like. In addition, stabilizers can be added to enhance the shelf life of the lotion composition such as cellulose derivatives, proteins and lecithin. All of these materials are well known in the art as additives for such formulations and can be employed, in appropriate amounts in the lotion compositions of the present invention.

There exists in the female body a complex process which maintains the vagina and physiologically related areas in a healthy state. In a female between the age of menarche and menopause, the normal vagina provides an ecosystem for a variety of microorganisms. Bacteria are the predominant type of microorganism present in the vagina; most women harbor about $10^9$ bacteria per gram of vaginal exudate. The bacterial flora of the vagina is comprised of both aerobic and anaerobic bacteria. The more commonly isolated bacteria are *Lactobacillus* species, corynebacteria, *Gardnerella vaginalis, Staphylococcus* species, *Peptococcus* species, aerobic and anaerobic *Streptococcal* species, and *Bacteroides* species. Other microorganisms that have been isolated from the vagina on occasion include yeast (*Candida albicans*), protozoa (*Trichomonas vaginalis*), mycoplasma (*Mycoplasma hominis*), chlamydia (*Chlamydia trachomatis*), and viruses (*Herpes simplex*). These latter organisms are generally associated with vaginitis or venereal disease, although they may be present in low numbers without causing symptoms. Physiological, social and idiosyncratic factors affect the quantity and species of bacteria present in the vagina. Physiological factors include age, days of the menstrual cycle, and pregnancy. For example, vaginal flora present in the vagina throughout the menstrual cycle can include lactobacilli, corynebacterium, ureaplasma, and mycoplasma. Social and idiosyncratic factors include method of birth control, sexual practices, systemic disease (e.g. diabetes), and medication. Bacterial proteins and metabolic products produced in the vagina can affect other microorganisms and the human host. For example, the vagina between menstrual periods is mildly acidic having a pH ranging from about 3.8 to about 4.5. This pH range is generally considered the most favorable condition for the maintenance of normal flora. At that pH, the vagina normally harbors the numerous species of microorganisms in a balanced ecology, playing a beneficial role in providing protection and resistance to infection and makes the vagina inhospitable to some species of bacteria such as *Staphylococcus aureus* (*S. aureus*). The low pH is a consequence of the growth of lactobacilli and their production of acidic products. Microorganisms in the vagina can also produce antimicrobial compounds such as hydrogen peroxide and bactericides directed at other bacterial species. One example is the lactocins, bacteriocin-like products of lactobacilli directed against other species of lactobacilli. Some microbial products may affect the human host. For example, *S. aureus* can produce and excrete into its environment a variety of exoproteins including enterotoxins, Toxic Shock Syndrome Toxin-1 (TSST-1), and enzymes such as proteases and lipase. There have been numerous attempts to reduce or eliminate pathogenic microorganisms and menstrually occurring TSS by incorporating into a tampon pledget one or more biostatic, biocidial, and/or detoxifying compounds. For example, L-ascorbic acid has been applied to a menstrual tampon to detoxify toxin found in the vagina of the human female during menstruation.

Incorporating glyceryl triacetate into a tampon pledget has been suggested. Others have incorporated monoesters and diesters of polyhydric aliphatic alcohols and a fatty acid containing from 8 to 18 carbon atoms. For example, glycerol monolaurate (GML) has been used to inhibit the production of *S. aureus* enterotoxins and TSST-1. However, as noted above, esterase is abundantly present in the vaginal epithelium and menstrual fluid. This esterase, in combination with esterase and lipase produced by bacteria can enzymatically degrade the esters into non-effective compounds. Until now, persons skilled in the art have not appreciated the affects of lipase and esterase on ester compounds.

U.S. Pat. No. 5,612,045 describes absorbent articles, such as catamenial tampons, for absorbing body fluids are disclosed which include an effective amount of a compound to substantially inhibit the production of exotoxins by Gram positive bacteria.

U.S. Pat. No. 4,405,323 to Auerbach discloses a tampon designed to eliminate the hazards of toxic shock syndrome and dysmenorrhea. The tampon has incorporated therein an antibacterial agent which is said to disperse on contact with body fluids and prevent development of the organisms which produce the toxins which cause toxic shock syndrome. Among the antibacterial materials disclosed for use are povidone-iodine compound, mercury, zinc, penicillin, erythromycin and nitrofurazone. (Povidone iodine is a topical preparation containing povidone and iodine, used for antisepsis of the skin.)

U.S. Pat. No. 5,201,326 describes a rod-shaped medical tampon for releasing an active substance, including (a) a tampon core of compressed fibers selected from the group consisting of cellulose fibers, cotton fibers, and acetate fibers; (b) a tampon cover surrounding said tampon core and being firmly bonded to one another by a glue, the tampon cover comprising a hardened collagen foam or a hardened gelatin foam impregnated with a retardant including a dissolved active substance to be released; and (c) a retrieval string connected to at least one of said tampon core and said tampon cover.

U.S. Pat. No. 4,722,937 method of prophylactics with respect to detoxification of *Staphylococcus aureus* and other toxins by ascorbic acid, salts and esters, topically applied by means of carriers which are otherwise regularly employed in the area where *Staphylococcus aureus* or other bacteria colonize, such as a pharmacological appliance including gauze pads, an absorbant mass or pad associated with menses, douches, and contraceptive compositions.

U.S. Pat. No. 4,675,014 describes method for absorbing bodily secretions while hindering the generation of odors and growth of microbes comprising applying a fibrous mass having copper cations bound through selected anions, preferably carboxymethyl, the amount of chemically bound copper being between 0.1 and 3% by weight. The fibrous mass can be in the form of a catamenial device, bandage, diaper, shoe liner, or the like.

SUMMARY OF THE INVENTION

A method, composition and article can be used for the application, association with or attachment to a surface, an open environment, a closed environment, an animal housing environment and/or the body of an animal (including humans). The composition may be provided directly, in a bulk composition or in an article that provides both absorbency and antimicrobial activity. The composition may be a dry or liquid composition. The article applied to the surface of an animal may be a diaper, gauze, padding, sanitary napkin, wrap, bandage, bandaid, surface covering (e.g., head rest cover, placemat, etc.) or the like and may comprise a water absorbent material; and a composition that reacts with water to produce molecular iodine. The composition provides a local concentration of at least 5 and preferably 10 parts per million iodine in alcohol and/or water carried to the surface or carried by the material. To fully activate the material there may be as little as 5% by weight solids in the activating water and/or alcohol (C1-C6 aliphatic, branched or cyclic alcohol) present respect to the total weight of the water absorbent material.

BRIEF DESCRIPTION OF THE FIGURES

FIG. 1 shows a view of the inside of an opened diaper product and the distribution of compositions according to the present technology.

DETAILED DESCRIPTION OF THE INVENTION

The composition of the present technology is activatable by contact with water, alcohol and/or alcohol/water compositions. The alcohols of primary consideration are the aliphatic and branched lower molecular weight alkanols such as methanol ethanol, propanol, iso-propnaol, butanol, t-butanol, i-butanol, penatnol, hexanol and the like in the one to six carbon atom length alcohols. The compositions have any of an antimicrobial activity, anti-odor activity, and the like and may oxidize harmful and/or toxic chemicals by release of the composition's active ingredients.

One way of providing molecular halide and especially molecular iodine ($I_2$) on site with a patient, rather than having to find a way of transporting it to a site) is to provide reactants that can readily produce molecular halogen and especially molecular iodine on-site in a controllable reaction. One format of providing the molecular iodine would be through the oxidation-reduction reaction between two salts o4r compounds to produce the molecular iodine. It is a readily controlled environment where the reaction can be performed in an aqueous environment. One reaction that can effect this would be generically described as:

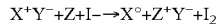
$$X^+Y^- + Z+I- \rightarrow X° + Z^+Y^- + I_2$$

In this reaction scheme, X is a metal (preferably a multivalent metal and more particularly a divalent metal), Y is an anion (preferably a multivalent anion and more preferably a divalent anion, and an anion having at least two oxygen atoms), Z is an alkali metal or alkaline cation. Examples of X are copper, iron, manganese, lead, nickel, tin, and the like, Y can be sulfate, sulfite, sulfonate, carbonate, phosphate, phosphate, nitrate, nitrie, borate, and the like, and Z can be sodium, lithium, potassium, ammonium, magnesium, aluminum, and the like. One preferred reaction would be:

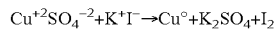
$$Cu^{+2}SO_4^{-2} + K^+I^- \rightarrow Cu° + K_2SO_4 + I_2$$

This reaction takes place readily in an aqueous environment and produces molecular iodine at a controlled rate. The reaction may be used by wetting, dispersing or dissolving the molecular iodide (in water, alcohol or water/alcohol compositions) and allowing the iodine in the carrying material be released and carried to the site (which may be a hard surface, a closed environment such as an oven, dishwasher, clothes washer, sterilization chamber, and the like, the carrying material itself, such as the fabric, clay, fibers, film etc.) penetrate the area intended to be treated. By applying the water or alcohol to a pad with the reagents therein, a hand applied sterilization wipe or wipe carried on a handle 9short length hand or broom length handle) for application of the sterilization material. By using such activatable wipes, the storage stability of the product is assured and the application of the active ingredients can be more easily made in a commonly acceptable format such as hand wipes, wipes on 0.2-1.0 meter handles, 0.8 to 2 meter handles, and even extendible handles for out-of-reach areas (such as 4 meter handles).

The iodine may persist for sufficient time to treat the area, particularly within a wetted material on the surface to be treated or a patient. Sufficient activating liquid (water, alcohol or mixture thereof, with or without additional active agents or ancillary agents) should be used so that at least some liquid is transferred to the surface being wiped. Even though at least a portion of the active iodine may be gaseous, it is desirable that the molecular iodine persist on a surface in many circumstances, which can be accomplished by the use of sufficient carrying liquid to persist for a few seconds or minutes on the surface, holding the molecular iodine in place to treat that surface.

The reaction may also be used by dispersing or mixing the two ingredients with alcohol or alcohol/water (e.g., in a spray container, a bucket, the fabric, fiber, film, sheet, etc.), either with additional water provided, with water of hydration on the first reactant (e.g., $X^+Y^-.nH_2O$, such as $CuSO_4.5H_2O$) or with ambient water in the carrying material. In the latter situation, water and/or alcohol may be carried in the wipe or fabric in frangible encapsulated beads so that pressure on the wipe can break the beads. Release the activating liquid, and the molecular halogen would be released without having to separately provide liquid. The two reactants may be physically separated from each other before being combined for application or reaction, as in separate capsules, coated particles, fibers, layers or the like.

The two reactants may be provided as a solid carrier medium that separates the two reactants until they are in contact with water (as in a soluble carrier such as polyvinyl alcohol, gelatin, amylase, sugars and the like, in pellet, fiber, dust, particle or block form). The two reactants may be independently coated with a soluble/dispersible coating and the two ingredients kept in a single water-penetrable layer.

Although the materials of the described technology may be provided in a vast array of materials and compositions applied to hard surfaces, closed small environments (up to 1.5 m³ in volume), closed medium environments (e.g., 1.5 m³ to 4.0 m³ in volume) to large closed environments (e.g., over 4.0 m³ in volume, such as rooms and offices), onto surfaces to be cleaned, soft surfaces such as apparel, hard surfaces such as countertops, toilets, wash basins, cook-tops, urinals, tools, instruments (including surgical instruments), operating surfaces, the surface (e.g., skin, hair) of patients, such as bandages, bandaids, diapers, gauze, wraps, sanitary napkins, tampons, plugs, sheet coverings 9e.g., on beds) and the like, the discussion will emphasize diapers and incontinence diapers for simplifying the disclosure, without intending to limit the scope of the invention.

The technology described herein is performed by applying the inactive materials and activating them, applying a recently activated material, or providing a solid carrier system to the target to be treated, whether an animate or inanimate target, such as the inanimate surfaces to be cleaned, sterilized, receive animal waste (especially urine, although moist feces can activate the materials) or treated, or a patient, and awaiting the presence of sufficient water (in solutions will also work, such as in urine), alcohol or water and alcohol to activate the ingredients and cause the gaseous iodine to form in sufficient concentration in the environment to be treated to attenuate, reduce or eliminate microbial activity such as bacterial growth, viral growth and the like in the treated area, such as the surface of the solid carrier. A simple format, in considering wipe-on applicators, bulk materials to be deposited on a surface (e.g., within an animal stall or cage) and sheet materials would include at least the following formats:

1) particulate and separate reactants may be carried in the same layer of the sheet or in individual particles in the bulk material;
2) particulate and separate reactants may be carried in different layers of the sheet or on different pieces of the bulk material (e.g., separate saw dust particles, separate straw pieces, separate absorbent particles, etc.);
3) particulate reactants may be carried in the same pellets in an anhydrous condition in the same layer of a sheet or on bulk material;
4) the particulate reactants may be adhered to the same or separate fibers or films that are associated with on constitute the sheet;
5) the reactants may be carried in fiber materials or particulates dispersed throughout or partially constituting the structure of the sheet or the bulk material;
6) absorbent particles may be blended with the reactant particles, with binders on one or both types of particles keeping the two types of particles evenly distributed (e.g., protective coatings one or both reagents cant bind the reagent particles to the absorbent particles);
7) capsules or microcapsules of the reactants in water-soluble or water-dispersible shells may be distributed throughout the sheet or bulk material; and
8) a film or films (water-soluble, water-dispersible or water-leachable) may carry one or more of the reactants, with the other reactant in a location that released or carried first reactant will be placed into contact with the second reactant in the presence of water and/or lower molecular weight alcohols.

Other formats and process may be used as long as the presence of water, alcohol or mixtures thereof on the applied active ingredients or carrier system enables the generation of gaseous molecular iodine within the carrier in sufficient concentration to act as a microbicide. It is possible to provide a paste material, with water-dispersible or alcohol-dispersible binding material (such as resins, high molecular weight organic liquid carriers (e.g., fatty acids, oliogmers, resins, etc.) that can be applied to a surface, with other additives 9abrasives, fragrances, brightening agents, thickening agents, antioxidants, UV protectors, etc.) to provide compositions with wider ranges of activity.

The process may use the above reaction to form the molecular iodine represented by $$XY + ZI \rightarrow X° + ZY + I_2$$ 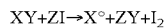

wherein X is a metal, Y is an anion, Z is an alkali metal or alkaline cation, or where X is a multivalent metal, Y is a multivalent anion, and Z is an alkali metal or alkaline cation, and is preferably represented by $$Cu^{+2}SO_4^{-2} + K^+I^- \rightarrow Cu° + K_2SO_4 + I_2.$$ 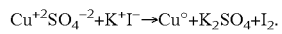

The process may be performed where the two reactants are carried as a solid, as coated materials, as blends of materials, in pouches, in capsules, in sheets or fabrics, as a preactivated liquid, or in a superabsorbent polymer. The solids carriers for the two reactants may also include compositions of the present that comprise superabsorbent or non-superabsorbent polymers, natural products (e.g., papers, cellulosic solids, water-insoluble porous materials which absorb or adsorb the film-forming material within the structure, water-soluble porous materials which absorb or adsorb the film-forming material within the structure, porous containers which merely slowly release a volume of the film-forming material, porous containers which both dissolve and physically release volumes of the film-forming composition through pores, and the like. In general, selection of an effective application rate can depend on habitat depth, surface debris, emergent and surface vegetation, organic matter, microbial and algal concentration, the specific target species, and the developmental stage of the target species. Superabsorbent polymers are described, by way of non-limiting examples in U.S. Pat. Nos. 6,403,674; 4,731,391. Superabsorbent polymers, including starch graft co-polymers, are known in the art. See, for example, those described in U.S. Pat. Nos. 4,375,535 and 4,497,930 (incorporated herein by reference), which have disclosed uses as adhesives, flocculants, sizes, water-retaining materials for agriculture and water-absorbing materials for sanitary materials. However, the spectrum of advantages attendant the use of superabsorbent polymers in solid and flowable terrestrial insecticidal, pesticidal or insecticidal/pesticidal delivery compositions have gone unrecognized.

The superabsorbent polymers that may be used in the practice of the present invention are synthetic organic polymers which are solid and hydrophilic, absorbing over 100 times their weight in water. These superabsorbent polymers are typically in a powder, granule, extruded, or flake form, adapted to be blended and/or agglomerated into any shape or form.

The superabsorbent polymers may be, for example, acrylamide alkali metal acrylate co-polymers; propenenitrile homo-polymers, hydrolyzed, alkali metal salts; polymers of propenamide and propenoic acid, alkali metal salts; hydrolyzed acrylonitrile co-polymers, and starch graft co-polymers and ter-polymers thereof. All of these are designed to be hydrophilic, absorbing over 100 times their weight in water. The resulting hydrophilic polymers can absorb from over one hundred to greater than about 5000, more typically around 500 to about 1,000, times their own weight in water (measured using distilled water, pH 7.5, 25, 760 mm Hg. absorption within about 30 seconds). However, the absorption or swelling capacity and absorption or swelling time typically varies with each specific superabsorbent polymer.

One class of superabsorbent polymers include combinations of a starch and organic monomers, oligomers, polymers, co-polymers or ter-polymers. They may be manufactured in a variety of ways, for example, the methods described in U.S. Pat. Nos. 4,375,535 and 4,497,930, and can be, for example, the product of grafting corn starch (amylopectin) with acrylonitrile (an acrylic monomer or oligomer). A second class of superabsorbent polymers includes combinations of acrylamide and acrylate polymers, co-polymers and ter-polymers.

The two reactants may be provided as a solid carrier medium or separate particulate materials that separate the two reactants until they are in contact with water (as in a soluble carrier such as polyvinyl alcohol, gelatin, amylase, sugars and the like, in pellet, fiber, dust, particle or block form). At least one of the two reactants may be independently coated with a soluble/dispersible coating and the two ingredients kept in a single water-penetrable layer. It is surprising that water-soluble or water-dispersible coatings or coverings (e.g., the stand-off particles) can be provided to the reagent particles without necessarily dissolving excessive amounts of a reagent. For example, simply by using a viscous water-soluble polymer (such as polyvinyl alcohol) in a rapidly coating/drying environment, any significant amount of dissolved reagent (e.g., KI dissolved in the polymer coating) will remain in the coating and also be active during any reaction. Unless substantial amounts of the dissolved material are on the surface of the coating, premature discoloring or premature reacting are still unlikely to occur, even if they might occur more easily than as compared to a completely encapsulated reactant.

Individually coated particles can be provided in water-soluble containers/coverings by using water-soluble or water-dispersible coating materials that are also organic solvent soluble (alcohol soluble) such as PVA, gels, polyvinylpyrrolidone, silica coatings, poly(ether ketones), poly(ester ketones), and the like are applied to the individual particles (one single reagent) or groups of particles (both or all reagents) and prilled, spray dried, or otherwise dried into separate, agglomerated, or packed coated particles. Polyvinyl alcohol may be coated on particles (even water soluble particles as used in the present technology) by use of particle coating technologies such as particle impacting in a fluidized bed or equivalent equipment such as shown in U.S. Pat. No. 6,037,019 (Kooyer).

A simple format, in considering application to agricultural fields for treatment to prevent nematodes or other ground or water-dwelling pests or for any age or stage of pest animal, would include at least the following formats:

1) Separate particulate with separate reactants may be carried in the same container;
2) particulate and separate reactants may be carried in different containers for subsequent separate or joint application;
3) particulate reactants may be carried in the same pellets in an anhydrous condition;
4) the particulate reactants may be adhered to the same or separate carrier materials such as pellets, abrasive particles, absorbent particles, bulk materials (straw, hay, bark, saw dust, etc.) or capsules;
5) the reactants may be carried in carrier materials dispersed throughout or partially constituting a separate carrier material;
6) capsules or microcapsules of the reactants in water-soluble or water-dispersible shells may be dispersed over the surface; and
7) a film or films (water-soluble, water-dispersible or water-leachable) may carry one or more of the reactants, with the other reactant in a location that released or carried first reactant will be placed into contact with the second reactant in the presence of water.

Other formats and process may be used as long as the presence of water or alcohol on the carrier system enables the generation of gaseous molecular iodine within the carrier in sufficient concentration to act as a sterilizing agent or pesticide.

A method of reducing odor in an animal housing environment (e.g., a stall, cage, litter box, pen and/or corral) is practiced by providing a reactive composition to the floor of the animal housing environment. The reactive composition is that as described generally herein, with at least two compounds that react in the presence of water and/or alcohol to produce molecular iodine. The at least two reagents may comprise at least two particulate reagents wherein at least one of the reagents as a particle coated with a water-soluble, water dispersible or water-penetrable covering that prevents ambient conditions of 50% relative humidity at 25° C. from causing more than 10% of the total of both reagents exposed to the ambient conditions from reacting in a twenty-four hour period while both reagents are present in a mixture. The at least two reagents may be mixed with water absorbent material prior to deposition onto the floor of the animal housing environment and then deposited onto the floor of the animal housing environment or mixed with the water absorbent material after its deposition onto the floor of the animal housing environment.

A water-soluble material actually disperses within the water in molecular size components (polymers are considered water-soluble even though the molecular components may have average molecular weights in the hundreds of thousands, e.g., 200,000 weight average molecular weight). A water dispersible covering may break up into small but microscopically visible (or visible with the naked eye) particles. A water-penetrable covering may be a discontinuous covering, such as a porous film, or massed particles covering the surface and allowing channels for liquid passage therethrough.

In the practice of this technology, these systems may be combined with existing technology such as litter box materials, stall bedding, cage bedding, and other absorbents used to control wastes from animals. Such materials may be natural materials as straw, chaff, bark, hay, sand, gravel, sawdust, cotton, and the like, and artifical materials such as kitty litter, synthetic absorbent particles (clay, bentonite, etc.), synthetic polymer fibers, starch materials, expanded cellulose fibers, expanded starch and the like. Fiber materials my include absorbing fibers and structural (strengthening) fibers such as natural materials, e.g., wool, cotton, hemp, rayon, paper, paper fluff, cellulose (including hardwood fibers, softwood fibers, processed pulp fibers, rice straw fibers, corn stover fibers, gyouli stick fibers, wheat straw fibers, starch fibers including various modified and extracted starch fibers), carbon, avian feathers, activated carbon and synthetic materials, e.g., polyester, nylon, plastics, polymers, copolymers, polypropylene, polyethylene, sodium polyacrylate, polyvinyl acetate. Combination fibers such as SAP (super absorbent polymer)/pulp fiber (about 400 micrometers) or SAP charged non-woven fibers can also be incorporated into the composite particles.

In general illustrative absorbent materials suitable for use as an animal litter that have an inherent ability to clump when wetted include but are not limited to "swelling" clays such as sodium smectite, sodium montmorillonite (aka sodium bentonite or Wyoming bentonite), beidellite, and hectorite.

Absorbent materials having little to no inherent ability to clump generally require the aid of a clumping agent to form a clumping litter material. Illustrative examples include non-swelling or poorly-swelling clays such as calcium smectite, calcium montmorillonite (calcium bentonite or Georgia White Clay), attapulgite (palygorskite), sepiolite, natural zeolite, synthetic zeolite, kaolinite, tobermorite, vermiculite, halloysite, illite, and mica; absorbent rocks such as perlite, volcanic ash, expanded perlite, pumice, diatomite (diatomaceous earth), tuff, opaline silica, slate, marls, and fossilized plant material; natural minerals such as opal (aka amorphous silica), silica, quartz (sand), calcite, dolomite, gypsum, bassenite (plaster of Paris), aragonite, and feldspar; synthetic minerals such as dicalcium silicate and amorphous silicas (e.g., silica gel, precipitated silica, fumed silica, silica aerogel) and aluminas (e.g., amorphous alumina, activated alumina, activated bauxite, gibbsite, bauxite, boehmite, pseudoboehmite). As used herein the terms "non swelling clays" and "poorly swelling clays" are synonymous. Other absorbent materials having little to no inherent ability to clump include straw, sawdust, wood chips, wood shavings, ground grain, porous polymeric beads, shredded paper, bark, cloth, ground corn husks, cellulose, water-insoluble inorganic salts, such as calcium sulfate, and sand. Reinforcing fiber attributes include the size, shape and activity of the fibers. Examples of fibers having beneficial shapes include bicomponent sheath core, bicomponent side by side, crimped fibers, bicomponent islands in the sea fibers. Examples of bicomponent fibers include fibers made of both polyethylene and polyester, or polyethylene and polypropylene. Nanofibers (i.e., fibers having at least one dimension in the nanometer size range) include those made through electrospinning techniques and bicomponent spitting techniques. Examples of active fibers include those with antimicrobial efficacy, water absorbing or (mass binding) and absorption rate efficacy, fragrance control release efficacy, and odor absorbing efficacy. These materials will be used alone or in combination with each other. Disclosure of such materials may be found, for example, in US Patent Publications 20080058739; 20080058738; 20080022939; 20070289543; 20070277739; 20060201438; 20060112894; 20060102085; and the like).

Research has shown that most cats prefer fine-grained litters, presumably because they have a softer feel. The new scoopable (clumping) litters usually have finer grains than the typical clay litter and are very popular. But high-quality, dust-free, clay litters are relatively small-grained and may be perfectly acceptable to your cat. Many cats are put off by the odor of scented or deodorant litters. For the same reason, it's not a good idea to place a room deodorizer or air freshener near the litter box. A thin layer of baking soda placed on the bottom of the box will help absorb odors without repelling your cat, and odors shouldn't really be a problem if you keep the litter box clean. An advantage of the present technology is the ability to avoid or eliminate the use of fragrances in or around the box, as the reagents are essentially odorless and the reacted materials have minimal to no odor and the iodine evaporates over brief time periods.

For particulates and fibers, clumping agents may be used. Some preferred clumping agent are methylcellulose (MC), methylhydroxyethylcellulose (MHEC), methylhydroxypropylcellulose (MHPC), guar gum, guar gum derivatives (such as hydroxypropyl guar and hydroxyethyl guar) and combinations thereof. Other water-soluble polymers (WSPs), such as carboxymethylcellulose (CMC), hydroxyethylcellulose (HEC), ethylhydroxyethylcellulose (EHEC), hydroxypropylcellulose (HPC), carrageenan, xanthan gum, alginate, and various combinations thereof can be used as secondary water-retention and clumping agents.

These materials may be used as bulk additives, in structured articles (pellets, bricks, fabrics and the like or in systems such as self-cleaning litter boxes (e.g., US Publication 20070039556). All references cited herein are incorporated by reference in their entirety.

The following examples are provided as prophetic descriptions of formats for delivery of technology according to the descriptions of the present invention.

Example 1

Fibers would extruded in a non-aqueous solvent of polyvinyl alcohol in two separate batches in combination with particulate reactants. One set of fibers would comprise 40% by weight of Copper Sulfate and the other set of fibers would comprise 40% by weight of Potassium Iodide. The two separate fibers would blended as 5% by total weight of fabric material into the fiber filled used in a diaper. The relatively low concentration (5%) of total added fiber would be expected to minimally change the properties expected from the fiber fill, except for the additional antimicrobial function, Upon activation by alcohol and/or water into the fibers, the polyvinyl alcohol would dissolve, the two reactants would dissolve in a single solution, the reactants would react, and the gaseous iodine would be produced.

The composition of the present technology provides a local concentration (in the water) of at least 5 ppm and preferably at least 10 parts per million iodine in water carried by the material (that is actual water and/or alcohol supported by the water absorbent material) when the material has 5% by weight of water and/or alcohol present in the water absorbent. The 5% is with respect to the total weight of water to the water absorbent material. The water and/or alcohol absorbing material preferably comprises water absorbing fibers. When providing alcohol, there is usually about 8% water present because of the difficulty in separating water from alcohol, except by expensive processing. The alcohol itself can provide additional anti-microbial activity, so the combination of alcohol and the molecular iodine is particularly effective in the practice of the present technology.

The composition that reacts with water and/or alcohol to form molecular iodine may comprise at least two salts, one of which at least two salts comprises an iodide salt. The at least two salts may be selected from the groups consisting of a) XY and b) Z I, wherein X is a metal, Y is an anion, and Z is an alkali metal, ammonium or alkaline cation. X is preferably a divalent metal cation. Y is preferably selected from carbonate, sulfate, sulfite, phosphate, phosphate, nitrate and nitrite, and Z is preferably selected from the group consisting of lithium, potassium, calcium, magnesium, sodium and ammonium. The composition that reacts with water to form molecular iodine preferably comprises cupric sulfate and potassium iodide.

The articles and compositions may have the iodine forming composition appropriately located within the article or evenly distributed throughout the applied material. For example, where the article is a hand-wipe sheet or diaper, it may have more than 70% of total composition in a central 50% of volume of the diaper. There is little need for antimicrobial activity on the portions of the diaper contacting the outer portions of the hips. Similarly, there would be little need for such activity along the waistband of the diaper. It is therefore desirable to concentrate the active materials in the diaper where the water (e.g., urine) is likely to be emitted. The iodine would migrate through the path of the water to all wetted areas.

A method of inhibiting microbial growth in an article provides a composition within the article, the composition comprising at lest two compounds that react in the presence of water to produce molecular iodine, and placing the article against the skin of an animal where an aqueous emission from the animal may occur. The method acts so that upon addition of water in an amount of between 10 and 100% by weight of the composition, a concentration of at least 10 parts per million of iodine is produced in the water in less than 15 minutes. The activity of the materials may be increased with respect to halogen releasing ability and volume by adding further halogen releasing components, especially iodates, chlorates, bromates, periodates, perchlorates and/or perbromates as a further reagent (e.g., as above 0% to 200% by weight of the further halogen-releasing components to KI. Metal, non-metal, alkaline and alkali halogens compounds may be used.

Another improvement would be to include starch materials into the composition or the surface to be treated so that the released iodine would cause the standard reaction for starch testing and a blue coloration would appear on the surface to alert caregivers that activation had occurred.

Example 2

Two porous films of water-soluble or water-dispersible material such as mannitol are extruded, the porosity provided by mechanical punching of the film of leaching of materials from the film, as well understood in the art. The separate films would contain 40% by weight of Copper Sulfate and 40% by weight of Potassium Iodide. The films can be used as adjacent or opposite side containers for the fiber fill (preferably with a separate non-dissolvable film).

Example 3

Individual granules of Copper Sulfate and Potassium Iodide are coated with water-soluble/dispersible coatings, preferably in the 2-8 micron thickness range. The uncoated particles would preferably have a diameter of between 5-50 microns so that they could be carried in fiber fill for a diaper without too ready settling out of the fiber fill. The coated particles are mixed into the fiber fill, either alone or with a tacky material (on the fiber or on the particles, such as a partially dried coating on the particles) to avoid separation. The fiber particle blend would constitute the fiber fill in a diaper.

FIG. 1 shows a view of the inside of an opened diaper product 20 and the distribution of compositions according to the present technology. The diaper product 20 is shown with a longitudinal center-line 100 and a horizontal center-line 110 about which are approximately symmetrically disposed wide panels 30, adhesive tabs 40, a central absorbent sheet 24, a stretchable/flexible outer cover layer 32 that may be continuous with the wide panels 30. A sectioned area 26 exposes longitudinal elastic filaments 54 that form the elasticity of the diaper along with the crinkling pattern 52. There are significant indentations 50 on the sides of the diaper t20 to allow fitting to legs. The central absorbent sheet 24 is shown with four separate areas 22 within which there could be the heaviest concentrations of the iodine forming material, and two panels 34 that are towards a more rearward placement on a user where lower concentrations of iodine forming material could be located. Areas outside the central absorbing sheet 24 may have little or no iodine forming materials therein. As noted above, the concentration of the iodine forming materials should be centralized where liquids are more likely to be emitted into the absorbent area and be retained in the absorbent area. The upper region of the diaper and pad 36 and the lower region of the diaper and pad 38 could therefore have less total amount and less concentration of the iodine forming materials then the central area 37. These concentration variations in the vertical direction may also be reflected or substituted with similar regional variations in the horizontal direction of the diaper 20.

The concentration of the iodine forming material may be selected in the article according the ultimate needs and designs of the manufacturer, and the level of ant-bacterial effect desired. The concentration of the iodine gas in the liquid in the absorbent material is one measure of the desired results, and a further measure of the desired results is referred to in the art as the kill percentage, a measure of the percent of a specific bacteria (e.g., $E.\ coli$) in a liquid sample that would be killed in 5 minutes by the level of active ingredient present. An example would be that the presence of about 8 parts per million of gaseous iodine dissolved in the aqueous material in the absorbent material would have a kill percentage over 50%. It would be desired, as noted above, to have higher concentrations of gaseous iodine in the liquid so that kill percentages are at least 60%, at least 70%, at least 80% and even at least higher than 90% for targeted bacteria and other microbes. Depending upon the specific bacteria or microbe selected for the measurement, the liquid may have to be provided with at least 5 or 10 parts per million (ppm), at least 15 ppm, at least 20 ppm, or at least 25 ppm by controlling the amount of reagents added, the rate of reaction of the reagents, and other controls aimed at keeping the iodine in solution in the liquid, such as providing thickening agents or other materials that would reduce the volatility of the iodine gas from the solution.

Example 3 (Prophetic)

Particles of KI would be impact coated with smaller particles (1/10 to 1/5 diameter ratio) of polyvinyl alcohol in accordance with the teachings of the processes and equipment shown in U.S. Pat. No. 6,037,019 (Kooyer). These PVA coated particles could then be mixed with particles of cupric sulfate with no concern for any immediate reaction between the salts, even in the presence of ambient moisture. These particles could be carried to the application site for admixture into water to provide iodine into other carrier material for application to conduit surfaces. It is important to appreciate that both water-borne iodine, alcohol-borne iodine and vapor-borne iodine can be produced in a single environment to address cracks, nooks and crannies in the surfaces to be treated or in the delivery system where intimate contact with water might be difficult.

Example 4 (Prophetic)

Particles of KI and $CuSO_4$ would be prepared by having "stand-off" particles of silica covering the surface of at least one of the particles. The particles could be applied by impact in a fluidized bed, electrostatic coating means, blending and other available methods known for the application of silica coatings to particles. These particles could be dusted or scattered onto stall or cage fill materials (e.g., straw, granules, sand, gravel, litter box fill, etc.) and placed onto the floor of the stall or cage.

The silica either allows free-flowing aqueous materials (e.g., urine, wash water, spilled drinking water, etc.) to pass through channels between individual particles to dissolve one or more of the KI and $CUSO_4$ or equivalent reagents, or actually completely disrupt the stand-off covering, so that the two reagents would then react to produce molecular iodine. Especially where the stall or cage material is absorbent, the liquid and some of the iodine would persist, to fight off odors and microbials. Additionally, the reaction would occur only locally where the liquid contacted the particles.

The coated/protected reagent materials may be added to existing stall materials (e.g., straw, sand, saw dust, clay, dirt, etc.) or may be combined with such materials that are added to the stall or cage prior to application to the floor of the stall.

As the molecular and high concentration of iodine in solutions has been proven to reduce odors and reduce microbial activity, they would be very effective anti-odor and anti-microbial agents in the animal housing field. This would also be effective in horse trailers and other transportation systems for animals, including live stock such as cattle, sheep, pigs, fowl (chicken and turkeys) and the like. One particular benefit in the livestock trade is that the treatment of the surfaces on which the animals walk would likely be able to reduce the need for direct provision of antibiotics into the livestock, which is a major environment and health concern.

Example 5 (Prophetic)

Protected particles of KI and $CuSO_4$ are blended with conventional retail kitty litter particles. This addition The activity of the materials may be increased with respect to halogen releasing ability and volume by adding further halogen releasing components, especially iodates, chlorates, bromates, periodates, perchlorates and/or perbromates as a further reagent (e.g., as above 0% to 200% by weight of the further halogen-releasing components to KI. Metal, non-metal, alkaline and alkali halogens compounds may be used.

All references cited herein are incorporated by reference in their entirety.

What is claimed:

1. An article for application to a surface to provide antimicrobial and/or anti-odor activity comprising:
   a water and/or ethanol absorbent porous fabric material; and
   a composition distributed within the porous fabric material of at least two particulate solid reagents that react in the presence of water and/or alcohol to produce molecular iodine,
   the composition capable of providing a local concentration of at least 5 parts per million iodine in water or ethanol carried by the material when the material has 5% by weight of water and/or alcohol present in the water and/or alcohol with respect to the total weight of the water and/or alcohol absorbent porous fabric material;
   wherein at least one of the two particulate solid reagents is coated with a water-soluble, water dispersible or water-penetrable solid covering of water-soluble or water-dispersible particles that physically separates the two particulate solid reagents and the solid covering prevents ambient conditions of 50% relative humidity at 25° C. from causing more than 10% of the total reagents exposed to the ambient conditions from reacting in a twenty-four hour period.

2. The article of claim 1 comprising a hand-wipe, wiping pad, mop head, diaper, sanitary pad, bandage, wound dressing or wrap.

3. The article of claim 1 where the water absorbing material comprises water absorbing fibers.

4. The article of claim 1 wherein the composition that reacts with water and/or C1 to C6 alcohol to form molecular iodine comprises at least two salts, one of which at least two salts comprises an iodide salt.

5. The article of claim 4 wherein the at least two salts are selected from the groups consisting of a) XY and b) Z I, wherein X is a metal, Y is an anion, and Z is an alkali metal, ammonium or alkaline cation.

6. The article of claim 5 wherein X is a divalent metal cation.

7. The article of claim 6 wherein Y is selected from carbonate, sulfate, sulfite, phosphate, phosphate, nitrate and nitrite.

8. The article of claim 7 wherein Z is selected from the group consisting of lithium, potassium, calcium, magnesium, sodium and ammonium.

9. The article of claim 1 wherein the composition that reacts with water and/or C1 to C6 alcohols to form molecular iodine comprises cupric sulfate and potassium iodide.

10. The article of claim 3 wherein the composition that reacts with water to form molecular iodine comprises cupric sulfate and potassium iodide.

11. The article of claim 1 wherein the at least two reagents comprise at least two particulate reagents wherein at least one of the reagents is a particle coated with a water-soluble, water-dispersible or water-penetrable solid covering that prevents ambient conditions of 50% relative humidity at 25° C. from causing more than 10% of the total reagents exposed to the ambient conditions from reacting in a twenty-four hour period wherein the solid coating comprises solid particles that form a water-soluble or water-dispersible solid covering as the particle covering.

12. The article of claim 1 wherein the composition that reacts with water to form molecular iodine comprises cupric sulfate and potassium iodide and wherein the at least two reagents comprise at least two particulate reagents wherein at least one of the reagents is a particle coated with a water-soluble, water-dispersible or water-penetrable solid covering that prevents ambient conditions of 50% relative humidity at 25° C. from causing more than 10% of the total reagents exposed to the ambient conditions from reacting in a twenty-four hour period.

13. The article of claim 3 wherein the composition that reacts with water to form molecular iodine comprises cupric sulfate and potassium iodide and wherein the at least two reagents comprise at least two particulate reagents wherein at least one of the reagents is a particle coated with a water-soluble, water-dispersible or water-penetrable solid particle covering that prevents ambient conditions of 50% relative humidity at 25° C. from causing more than 10% of the total reagents exposed to the ambient conditions from reacting in a twenty-four hour period while both reagents are present in a mixture the porous fabric comprising a polymeric or cellulosic fabric.

14. The article of claim 12 wherein absorbent clay particles are present within the porous fabrics and a clumping agent is blended with the composition that reacts with water and the absorbent clay particles, and the clumping agent is a different material from the absorbent clay particles.

15. The article of claim 13 wherein absorbent clay particles are present within the porous fabrics and a clumping agent is blended with the composition that reacts with water and the absorbent clay particles, and the clumping agent is a different material from the absorbent clay particles.

* * * * *